United States Patent [19]

Soukup

[11] Patent Number: 5,152,299
[45] Date of Patent: Oct. 6, 1992

[54] IMPLANTABLE ENDOCARDIAL LEAD WITH SPRING-LOADED SCREW-IN FIXATION APPARATUS

[75] Inventor: Thomas M. Soukup, Lake Jackson, Tex.

[73] Assignee: Intermedics, Inc., Angleton, Tex.

[21] Appl. No.: 688,036

[22] Filed: Apr. 19, 1991

[51] Int. Cl.⁵ ............................................. A61N 1/05
[52] U.S. Cl. ................................. 128/785; 128/786; 128/642; 128/419 P
[58] Field of Search ............................... 128/784–786, 128/419 P, 642

[56] References Cited

U.S. PATENT DOCUMENTS

| | | | |
|---|---|---|---|
| 4,217,913 | 8/1980 | Dutcher | 128/785 |
| 4,452,254 | 6/1984 | Goldberg et al. | 128/785 |
| 4,498,482 | 2/1985 | Williams | 128/419 P |
| 4,649,938 | 3/1987 | McArthur | 128/785 |
| 4,886,074 | 12/1989 | Bisping | 128/785 |
| 4,934,371 | 6/1990 | Malis et al. | 128/785 |
| 4,967,766 | 11/1990 | Bradshaw | 128/785 |
| 5,003,992 | 4/1991 | Holleman et al. | 128/785 |
| 5,076,285 | 12/1991 | Hess et al. | 128/785 |

Primary Examiner—Lee S. Cohen
Assistant Examiner—J. R. Jastrzab
Attorney, Agent, or Firm—John R. Merkling

[57] ABSTRACT

An implantable endocardial lead with retractable sharpened helix. The piston has a central bore for receiving a specialized stylet. The stylet comprises a flexible wire having an enlarged distal end or tip. An elastomeric sliding sleeve fits over the wire. When the proximal end of the stylet is inserted into the bore in the piston, the wire can be withdrawn slightly, pulling the enlarged tip into the tube, and wedging the tube against the walls of the bore. By manipulating the stylet, the helix can be exposed outside of the lead, or retractable into the lead, as desired.

12 Claims, 1 Drawing Sheet

IMPLANTABLE ENDOCARDIAL LEAD WITH SPRING-LOADED SCREW-IN FIXATION APPARATUS

BACKGROUND OF THE INVENTION

1. Field of the Invention

My invention relates generally to cardiac stimulation, and more particularly to an implantable endocardial lead which stimulates or senses electrical activity of the heart and which employs a spring-loaded fixation mechanism comprising a sharpened helix which screws itself into cardiac tissue without rotation of the lead or a stylet.

2. Prior Art

There are generally two types of body implantable leads used with cardiac pacemarkers—one which requires surgery to expose the myocardial tissue to which an electrode is affixed and another which can be inserted through a body vessel, such as a vein, into the heart where an electrode contacts the endocardial tissue. In the latter type, the endocardial lead is often secured to the heart through the endothelial lining by a sharpened helix affixed to a distal end of the lead. When the end of the lead contacts the lining of the heart at a desired location, the lead may be secured in place by rotating the lead, thus screwing the helix into the heart tissue.

A helix system has been relatively effective in secureing an endocardial lead once the initial location of the lead has been achieved. However, it is undesirable to expose the sharpened helix while the lead is being inserted through a blood vessel into the heart. Moreover, to implant the helix into the heart, it has generally been proposed that the helix be rotated either by rotating the entire lead or by rotating a stylet or other structure within the lead.

For example, the following patents illustrated leads wherein the helix is rotated by the rotation of the entire lead: U.S. Pat. No. 3,974,834 to Kane; U.S. Pat. No. 4,570,642 to Kane, and Revane; U.S. Pat. No. 4,649,938 to McArthur; U.S. Pat. No. 4,924,881 to Brewer and U.S. Pat. No. 4,967,716 to Bradshaw.

U.S. Pat. No. 4,463,765 to Gold for a "Screw-in Pacing Lead Assembly", on the other hand, illustrates the use of an internal structure to rotate the helix. A flat ribbon extending throughout the lead from a proximal to a distal end thereof is disclosed. Another internal apparatus is disclosed in U.S. Pat. No. 5,056,516 to Paul R. Spehr. An endocardial lead with a flexible, tubular landyard is described. The lanyard passes through a lumen from a proximal end of the lead to a distal end of the lead where the lanyard was attached to a sliding member supporting a helix. When the helix is in an exposed position, torque can be transmitted from the proximal end of the lanyard from the distal end thereof through the piston and then to the helix to screw the helix into the endocardial tissue.

Other apparatus for securing an electrode within the heart are also known. For example, U.S. Pat. No. 3,754,555 to Schmitt discloses a lead having prongs which can be thrust out from and retracted into an electrode, U.S. Pat. No. 4,858,623 to Bradshaw and Baker discloses a lead having a pivoting rigid hook. In a first position, the hook is collapsed against the electrode and not exposed to tissue. In a second position, the hook is extended and can engage a cardiac wall.

SUMMARY OF MY INVENTION

My present invention provides an implantable endocardial lead with a spring-loaded screw-in fixation means. In the preferred embodiment, the fixation means comprises a sharpened helix with ia attached to a torsion spring in tension and retracted within an electrode at a distal end of the lead. The lead defines a lumen from its proximal to its distal end. A stylet can be inserted into the lumen at the proximal end and passed through the lead to the distal end. Located at the distal end of the lead is a piston joining the sharpened helix to the compression spring. The spring forces the piston away from the distal end of the lead. Before insertion of the lead into the heart, the spring can be loaded in torsion, preferably by using a specialized stylet. The tension of the torsion spring locks the piston and attached helix in a selected position. During insertion, therefore, there is a predetermined load on the spring.

To expose the sharpened helix, a stylet presses against a proximal end of the piston, extending the spring. When the piston is disengaged from a locking means and the distal end of the lead is pressed against the cardiac wall, the helix is rotated into the wall by the spring. It is not necessary to rotate either the lead or an internal structure such as a stylet, lanyard or coil ribbon. After insertion of the helix the stylet can then be removed.

With the foregoing in mind, it is an object of my invention to provide an endocardial lead with means for driving a sharpened helix into a cardiac wall.

It is a principal object of my present invention to provide an implantable endocardial lead with a fixation means which can implant itself into a cardiac wall without rotary manipulation of either the lead or an internal structure.

A further object of my invention is to provide a lead wherein the fixation means is rotated by a preloaded torsion means.

It is another object of my invention to provide a spring-loaded fixation means on a lead wherein the spring force is not transmitted to the cardiac wall when the lead is attached thereto.

These and other objects and features of my invention will be apparent from the detailed description taken with reference to the accompanying drawings.

DETAILED DESCRIPTION OF THE PREFERRED EMBODIMENT

Figure 1:
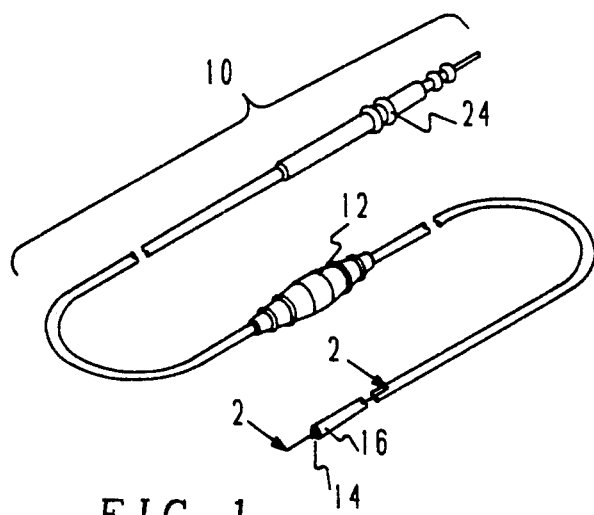
FIG. 1 is a perspective view of an implantable endocardial lead according to my invention.

I will now describe my preferred embodiment of my invention with reference to the drawings. Like numerals will be used to designate like parts throughout. FIG. 1 shows an endocardial lead, generally designated 10. The lead 10 has a suture sleeve 12 which slides along the lead 10 and which can be attached at an entrance into a vein of a patient in a conventional manner. The lead 10 also has an electrode 14 located at a distal tip 16 of the lead.

Figure 2:
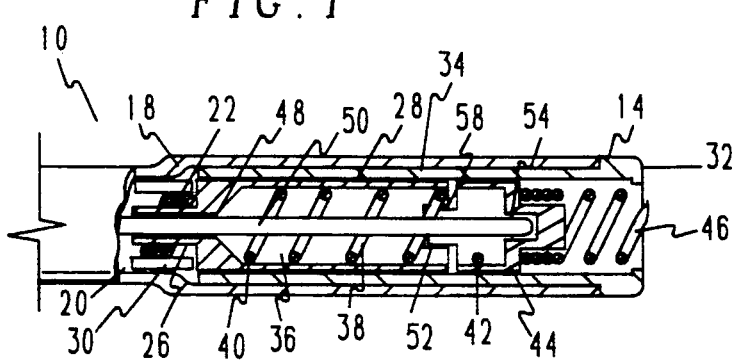
FIG. 2 is a sectional view of a distal tip of the lead taken along line 2—2 of FIG. 1.
Figure 3:
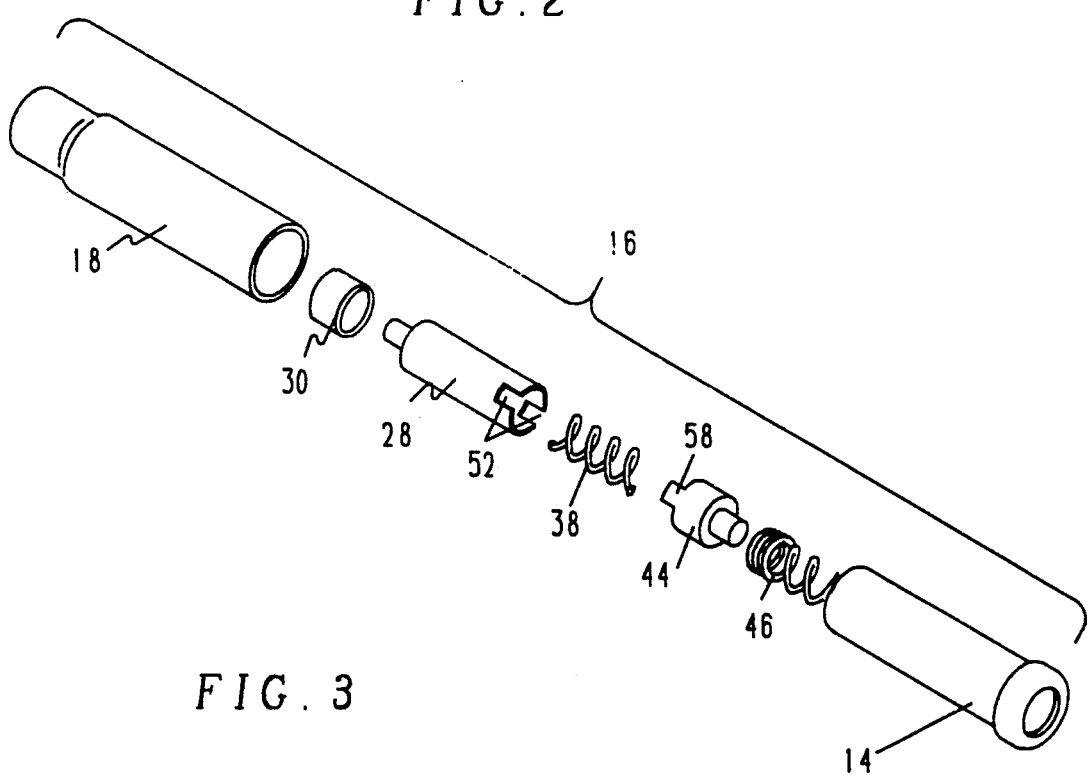
FIG. 3 is an exploded perspective view of the distal tip.

As shown in FIG. 2, the lead 10 comprises a silicon or polyurethane sheath 18 which defines a lumen 20 along a longitudinal axis of the lead 10. Within the lumen 20, there is a coil conductor 22 for transmitting electrical impulses between the electrode 14 and a proximal end 24 of the lead 10. In the illustrated embodiment, a trifilar conductor is shown as the coil conductor 22. The coil conductor 22 wraps around a crimp slug 26 at a proximal end of a spring housing 28. A cylindrical crimp connector 30 surrounds the crimp slug 26 and a portion of the coil conductor to provide electrical contact and mechanical fixation.

The electrode 14 comprises a ring contact 32 and a conductive sleeve 34. The conductive sleeve 34 fits tightly over a distal end of the spring housing 28. The sheath 18 encloses the conductive sleeve 30 of the electrode 14 to the ring contact 32.

Within the spring housing 28 there is a cylindrical chamber 36 which houses a torsion spring 38. The torsion spring 38 is secured to the spring housing at a proximal end 40 of the spring. A distal end of the spring 42 is secured to a piston 44 which supports a sharpened helix 46. At the proximal end of the spring housing 28 there is a bore 48 providing access for a stylet 50. One or more notches 52 (preferably more than one notch) are provided at the distal end of the spring housing 28 for inhibiting rotation of the piston 44. The piston 44 has an internal slot 54 which is adapted to receive a flattened end of specialized stylet so that the piston can be rotated. At a proximal end of the piston 44, one or more tabs 58 are provided. The tabs 58 engage the slots 52 in the spring housing.

In my preferred embodiment a specialized stylet being a flattened end is inserted into the lead, through the lumen, into the spring housing thence into the slot in the piston. By pushing on the stylet, the piston 44 is moved distally so that the tabs disengage from the slots in the spring housing. The stylet can then be rotated, turning the piston and preloading the torsion spring 38. When the piston has been turned sufficiently to compensate for the desired number of turns in the sharpened helix 46, the stylet can be withdrawn. As the stylet is withdrawn, the spring 38 pulls the piston 44 against the spring housing 28. The tabs 58 lock into the slots 52 preventing the torsion spring 38 from turning the piston.

To engage the fixation means, the lead is inserted into the heart and the electrode 32 is pressed against the cardiac wall. The stylet is inserted into the lead and pressed against the piston, moving the piston and helix distally. As the helix 46 is exposed outside of the electrode 14 and pressed against the cardiac wall, the tabs 58 disengage from the slots 52 and the torsion spring 38 acts to screw the helix into the wall of the heart.

My invention may be embodied in other specific forms without departing from the spirit or essential characteristics thereof. The present embodiment is therefore considered in all aspects as illustrative and not restrictive, the scope of the invention being indicated by the appended claims rather than by the foregoing description, and all changes which come within the means and range of equivalency of the claims are therefore intended to be embraced therein.

I claim as my invention:

1. A lead assembly for implantation in a patient, the assembly comprising:
   an electrode adapted for insertion into a chamber of the patient's heart for electrical stimulation thereof and having a lumen extending through the electrode from a proximal end to a distal end thereof;
   a lead having a sheath and a conductor, said conductor connected to said proximal end of the electrode at a distal end of the lead and adapted to transmit electrical impulses between the electrode and a proximal end of the lead, the lead having a lumen extending through the lead from the proximal end to the distal end thereof; and
   means for securing the electrode to the lining of the heart chamber, the securing means being in the lumen of the electrode and having
      fixation means for penetrating the lining of the heart,
      spring means for rotating said fixation means, and
      means for releasing said spring means to permit rotation of said fixation means.

2. The lead assembly according to claim 1 further comprising means for pre-loading said spring means.

3. The lead assembly according to claim 1 wherein the fixation means comprises a sharpened helix.

4. The lead assembly according to claim 3 wherein said spring means have a proximal and a distal end and wherein means for releasing said spring means comprise
   a piston attached to said sharpened helix and to said distal end of said spring means,
   a housing attached to said proximal end of said spring means, and
   means for selectively securing said piston to said housing.

5. The lead assembly according to claim 4 further comprising means for pre-loading said spring means.

6. The lead assembly according to claim 5 wherein the pre-loading means comprise a stylet and means for turning said piston.

7. The lead assembly according to claim 6 wherein the piston has a slot thereon and the stylet has a flattened distal tip for engaging said slot on said piston.

8. The lead assembly according to claim 4 wherein the selectively securing means comprise at least one tab and a mating slot.

9. The lead assembly according to claim 8 wherein the piston has a proximal side and said tab is carried on said proximal side and said housing has a distal side and said mating slot is in said distal side.

10. The lead assembly according to claim 9 further comprising means for pre-loading said spring means.

11. The lead assembly according to claim 10 wherein the pre-loading means comprise a stylet and means for turning said piston.

12. The lead assembly according to claim 11 wherein the prison has a slot thereon and the stylet has a flattened distal tip for engaging said slot on said piston.

* * * * *